United States Patent [19]

Robbins

[11] 4,440,695
[45] Apr. 3, 1984

[54] METHOD FOR PREPARATION OF N-PHOSPHONOMETHYLGLYCINE

[75] Inventor: Jeffrey D. Robbins, Berkeley, Calif.

[73] Assignee: Stauffer Chemical Company, Westport, Conn.

[21] Appl. No.: 407,366

[22] Filed: Aug. 12, 1982

[51] Int. Cl.³ .............................................. C07F 9/38
[52] U.S. Cl. ........................................... 260/502.5 F
[58] Field of Search ................................. 260/502.5 F

[56] References Cited

U.S. PATENT DOCUMENTS 3,288,846 11/1966 Irani et al. .................... 260/502.5 E
3,907,652 9/1975 Wagenknecht et al. ..... 260/502.5 F
4,131,448 12/1978 Franz ............................ 260/502.5 F Primary Examiner—J. E. Evans
Attorney, Agent, or Firm—Paul R. Martin

[57] ABSTRACT

A method for the production of N-phosphonomethylglycine which comprises reacting N,N-bis(phosphonomethyl)glycine having the formula

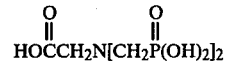

with glycine in the presence of a hydrogen ion donor and of water, and at a sufficient temperature and at a sufficient pressure to cause the reaction to go to completion.

10 Claims, No Drawings

METHOD FOR PREPARATION OF N-PHOSPHONOMETHYLGLYCINE

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are incorporated into the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof.

In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., December 8, 1964) is to react N-phosphinomethylglycine (glycinemethylenephosphinic acid) with mercuric chloride in a water solvent at reflux temperature, and subsequently separating the reaction products. Another method is the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as a herbicide, other methods of making the compounds are constantly being sought in order to provide improved or alternate methods of manufacture.

SUMMARY OF THE INVENTION

It has now been discovered that N-phosphonomethylglycine can be produced by reaction of N,N-bis(phosphonomethyl)glycine with glycine, in the presence of water, a hydrogen ion donor, and with accompanying heat. The formula for this reaction can be represented as follows:

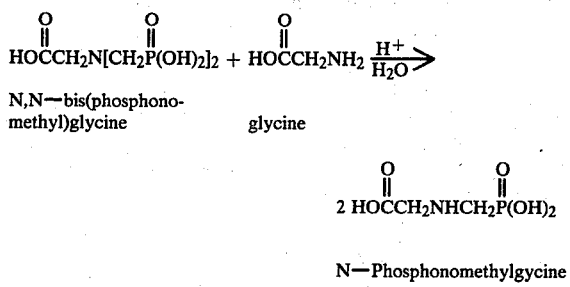

N,N—bis(phosphonomethyl)glycine    glycine

N—Phosphonomethylgycine

The reaction is carried out under such conditions of time, temperature and pressure that the maximum amount of end product is formed.

The hydrogen ion donor is preferably an acid selected from the group consisting of hydrochloric acid, hydrobromic acid, and hydriodic acid, with hydrochloric acid being the most preferred.

The water serves as a solvent for the reactants.

Preferably, the reaction is carried out at temperatures ranging from about 100° to about 150° C., most preferably 125°–135° C., and at pressures ranging from about 3 to about 10 atmosphere in the case of hydrochloric acid as the hydrogen ion donor and 1 to 3 atmospheres in the case of hydrobromic acid.

This invention will be better understood by reference to the specific examples which follow, which serve to illustrate the instant invention.

EXAMPLE 1

Preparation of N-Phosphonomethylglycine

To a 50 milliliter (ml) three-necked, round-bottom flask equipped with a magnetic stirrer, a heating mantle, a condenser, and a thermometer was added 2.6 grams (g) (10.0 mole) of N,N-bis(phosphonomethyl)glycine, 9 g (10 mmole) of glycine hydrochloride, and 5 ml of 47% aqueous hydrobromic acid. The solution was then heated to reflux temperature which was approximately 123° C., and was refluxed for a period of 15.5 hours. Thereafter, the solution was cooled, and a sample taken for quantitative analysis by high performance liquid chromatograhy (hplc). The yield of N-phosphonomethylglycine was 2.0 mmole (10% of theory).

EXAMPLE 2

Preparation of N-Phosphonomethylglycine

To a Teflon ® lined 300 ml pressure vessel was charged 1.5 g (20 mmole) of glycine, 5.2 g (20 mmole) of N,N-bis(phosphonomethyl)glycine, and 20 ml of 37% aqueous hydrochloric acid. The mixture was heated with agitation at 6.5–7.5 atmospheres of pressure and 128°–131° C. for 5.0 hours. The cooled reaction mixture was sampled for quantitative analysis by hplc. The yield of N-phosphonomethylglycine was 4.9 mmole (12% of theory).

While it is possible to omit the glycine from the reaction as indicated above, because the N,N-bis(phosphonomethyl)glycine does in fact hydrolyze to N-phosphonomethylglycine under the reaction conditions as given, it has been found that the yields are better with the glycine present, and for that reason it is preferred to conduct the reaction with the glycine added.

The N-phosphonomethylglycine which is produced in accordance with the method of the invention, in and of itself, has herbicidal and plant growth regulating efficacy. However, because the acid form is not in itself very soluble in aqueous solutions, it is preferred to convert this compound into one of its salts for inclusion into herbicidal compositions. The salt form can be produced by reacting the acid with a suitable base. A salt which has been found to have a high rate of herbicidal activity and plant growth regulating activity is the trialkylsulfonium salt of N-phosphonomethylglycine, such as is disclosed in U.S. Pat. No. 4,315,765.

The mole ratio of N,N-bis(phosphonomethyl)glycine to hydrogen ion donor used in the reaction of the invention can range from about 1 to 10 to about 1 to 20, with the preferred ratio being from about 1 to 12. When glycine is additionally added to the reactants, the preferred mole ratio of N,N-bis(phosphonomethyl)glycine to glycine is from about 1 to 0.5 to about 1 to 2, with the most preferred ratio being 1 to 1.

The reaction can be carried out at pressures ranging from 1 atmosphere to 10 atmospheres. When hydrochloric acid is the hydrogen ion donor, the reaction pressure preferably ranges from 3 to 10 atmospheres, while when hydrobromic acid is the hydrogen ion donor, the reaction can be carried out at from 1 to 3 atmospheres.

Variations in the reaction conditions of time, temperature, and pressure can be made without departing from the spirit and scope of the invention as claimed.

What is claimed is:

1. A method for the production of N-phosphonomethylglycine which comprises reacting N,N-bis(phosphonomethyl)glycine, having the formula

with hydrochloric acid in the presence of water, and at a sufficient temperature and at a pressure ranging from about 3 to about 10 atmospheres sufficient to cause the formation of N-phosphono-methylglycine.

2. The method of claim 1 which additionally includes glycine as a component of the reaction mixture.

3. The method of claim 1 in which the temperature of the reaction ranges from about 100° to about 150° C.

4. A method for the production of N-phosphonomethylglycine which comprises reacting N,N-bis(phosphonomethyl)glycine of the formula

with glycine, and a hydrogen ion donor in the presence of water, and at a sufficient temperature and pressure and for a sufficient period of time for the reaction to go to completion, wherein the mole ratio of N,N-bis(phosponomethyl)glycine:glycine:hydrogen ion donor ranges from about 1:1:10 to about 1:1:20.

5. The method of claim 4 in which the hydrogen ion donor is selected from the group consisting of hydrochloric acid, hydrobromic acid or hydriodic acid.

6. The method of claim 5 in which said hydrogen ion donor is hydrochloric acid.

7. The method of claim 5 in which said hydrogen ion donor is hydrobromic acid.

8. A method for the production of N-phosphonomethylglycine which comprises reacting N,N-bis(phosphonomethyl)glycine, having the formula

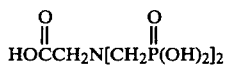

with hydrobromic acid in the presence of water, and at a sufficient temperature and at a pressure ranging from about 1 to about 3 atmospheres sufficient to cause the reaction to go to completion.

9. The method of claim 8 which additionally includes glycine as a component of the reaction mixture.

10. The method of claim 8 in which the temperature of the reaction ranges from about 100° to about 150° C.

* * * * *

UNITED STATES PATENT AND TRADEMARK OFFICE
CERTIFICATE OF CORRECTION

PATENT NO. : 4,440,695
DATED : April 3, 1984
INVENTOR(S) : Jeffrey D. Robbins

It is certified that error appears in the above-identified patent and that said Letters Patent is hereby corrected as shown below:

In Column 4, Claim 4, the phrase beginning "and for a sufficient period of time for the reaction to go to completion..." should read --- and for a sufficient period of time to cause the formation of N-phosphonomethyl-glycine,... ---

Signed and Sealed this

Twelfth Day of March 1985

[SEAL]

Attest:

DONALD J. QUIGG

Attesting Officer    Acting Commissioner of Patents and Trademarks